United States Patent
Chambers et al.

(10) Patent No.: US 9,227,989 B2
(45) Date of Patent: Jan. 5, 2016

(54) CALCIUM TREATMENT OF ALKYL-TIN STABILIZERS

(71) Applicant: AXIALL CORPORATION, Atlanta, GA (US)

(72) Inventors: Scott Chambers, Goshen, CT (US); Davide Achiluzzi, Maple (CA); Chris Turnbull, Barrie (CA); Anna Jankowski, Barrie (CA)

(73) Assignee: Royal Group, Inc., Atlanta, GA (US)

( * ) Notice: Subject to any disclaimer, the term of this patent is extended or adjusted under 35 U.S.C. 154(b) by 0 days.

(21) Appl. No.: 14/516,615

(22) Filed: Oct. 17, 2014

(65) Prior Publication Data

US 2015/0112006 A1    Apr. 23, 2015

Related U.S. Application Data

(60) Provisional application No. 61/892,805, filed on Oct. 18, 2013.

(51) Int. Cl.
*C07F 7/22* (2006.01)

(52) U.S. Cl.
CPC .................................. *C07F 7/2296* (2013.01)

(58) Field of Classification Search
CPC ....................................................... C07F 7/2296
See application file for complete search history.

(56) References Cited

U.S. PATENT DOCUMENTS

| | | | |
|---|---|---|---|
| 2007/0054086 A1* | 3/2007 | Pagel | C08K 5/0008 428/106 |
| 2008/0090920 A1* | 4/2008 | Maxwell | C08J 9/0019 521/79 |

* cited by examiner

*Primary Examiner* — Robert Harlan
(74) *Attorney, Agent, or Firm* — Hunton & Williams, LLP

(57) ABSTRACT

An alkyl-tin stabilizer composition is treated with a calcium compound to reduce the carboxylate content level of the stabilizer.

20 Claims, No Drawings

CALCIUM TREATMENT OF ALKYL-TIN STABILIZERS

CROSS-REFERENCE TO RELATED APPLICATIONS

The present application claims priority to U.S. Provisional Application No. 61/892,805 filed Oct. 18, 2013, the contents of which are incorporated herein by reference in their entirety.

BACKGROUND OF THE INVENTION

During the manufacture of alkyl-tin thioglycolate stabilizers a production side reaction leads to the formation of the undesirable respective alkyl-tin salt of thioglycolic acid ("TGA"). The alkyl-tin salt of TGA is a degradation product of the ester (thioglycolate) and may form a ring structure. Typically these salts are referred to as carboxylates. Alkyl-tin salts of TGA have limited solubility in their respective alkyl-tin thioglycolate stabilizers and when present in sufficient quantities, they may cloud the stabilizer and result in precipitate formation. The precipitate formation may not necessarily occur immediately during the production process and may occur after the stabilizer is allowed to stand for a period of time. The cloudiness in the stabilizer caused by the alkyl-tin salts of TGA is undesirable to both end users and manufacturers.

DETAILED DESCRIPTION OF THE INVENTION

In an exemplary embodiment of this invention, a finished butyl-tin thioglycolate stabilizer containing undesirable levels of butyl-tin salt of TGA is treated by adding calcium oxide (CaO) and/or calcium hydroxide (Ca(OH)2) to the stabilizer. The reaction mixture is then filtered, which results in a clear butyl-tin thioglycolate stabilizer that has lower carboxylate levels and is bench stable for further carboxylate precipitation. This process is applicable to other alkyl-tin thioglycolate stabilizers (e.g. methyl-tin thioglycolate stabilizers, octyl-tin thioglycolate stabilizers, etc.), as well as the butyl-tin thioglycolate stabilizer presented in this exemplary embodiment.

In some embodiments this treatment may also produce the desirable property of aiding in removing coloring in the alkyl-tin stabilizer which is also desirable to end users and manufacturers.

In an embodiment of the invention, CaO and/or Ca(OH)2 is mixed with the alkyl-tin stabilizer either in situ and then filtered. In alternative embodiment the CaO and/or Ca(OH)2 may be added to the filter media prior to filtering the alkyl-tin stabilizer, though adding the CaO and/or Ca(OH)2 to the filter media may be a less efficient method Anhydrous sodium sulfate ("anhydrous Na2SO4") may also be added to the filter media to aid in removing any water that may be present and/or created.

In some embodiments, approximately 0.25 to 5% CaO and/or Ca(OH)2 by weight of alkyl-tin stabilizer may be used in the treatment of an alkyl-tin stabilizer. Adding CaO and/or Ca(OH)2 in levels lower than this range resulted in little effectiveness in lowering carboxylate levels, and higher levels of CaO and/or Ca(OH)2 were no more effective than the 0.25 to 5% range.

In some embodiments, the treatment may be carried out at ambient temperature. In other embodiments, the treatment may be carried out at elevated temperatures (50-60° C.). Treatment may be effective over the entire range of temperatures described. In a preferred embodiment, the treatment is performed at the higher end of the temperature range (~60° C.), as many chemical reactions are faster at higher temperatures.

In one embodiment, CaO was added to the alkyl-tin stabilizer and it effectively reduced the carboxylate level in test samples of stabilizer. This was a surprising and unexpected result. It also effectively reduced the strong color in the alkyl-tin stabilizer.

In another embodiment, Ca(OH)2, which is a more reactive product due the better leaving group, i.e. water, was used to treat the alkyl-tin stabilizer. The Ca(OH)2 effectively worked here using about 1% by weight of alkyl-tin stabilizer. Prior to treatment with Ca(OH)2 the alkyl-tin stabilizer was estimated to contain about 1.3% carboxylate as determined by Fourier transform infrared spectroscopy ("FTIR"), and resulted in carboxylate level of <0.3% after treatment.

Though both CaO and Ca(OH)2 may be used in embodiments of this invention to reduce carboxylate levels in alkyl-tin stabilizers, it was found that Ca(OH)2 may be less effective at reducing the coloring in alkyl-tin stabilizers.

In some embodiments of the invention a combination of the CaO:Ca(OH)2 at ratios of 1:1 to 1:5 by weight may be used to effectively treat carboxylate levels and coloring in alkyl-tin stabilizers. These embodiments were made by mixing the CaO or Ca(OH)2 together with the stabilizer and then filtering the mixture until clear. In some embodiments a centrifuge may be used to reduce filtration time.

In other embodiments the CaO and Ca(OH)2 may be added to filter media. The filter media may include a combination of CaO, Ca(OH)2, anhydrous Na2SO4 (to remove water in the alkyl-tin stabilizer) and Celite (diatomaceous earth) and/or other typical filter media. In one embodiment the ratios of the components (CaO:Ca(OH)2: anhydrous Na2SO4:Celite) in the filter media is 1.5:1.5:3:3 by weight (i.e. ⅓ CaO and Ca(OH)2, ⅓ anhydrous Na2So4, and ⅓ Celite). alkyl-tin stabilizer may then be filtered through the disclosed filter media to reduce carboxylate levels in the alkyl-tin stabilizer. In some embodiments the alkyl-tin stabilizer may make successive passes through the filter media to further increase the effectiveness of reducing the carboxylate level in the alkyl-tin stabilizer. In some embodiments the carboxylate level in the alkyl-tin stabilizer after filtering may be determined by FTIR, by those of ordinary skill in the art.

In a further embodiment filter media including a 5:1:2 ratio by weight of (CaO:Ca(OH)2: anhydrous Na2SO4) was used. Successive replacement of the filters and the filter media was employed when the filter media would clog (typical) and eventually resulted in a low carboxylate levels in the stabilizer (~0.4%) and had a color better than the untreated alkyl-tin stabilizer. The proportion of calcium used was less than 1% by weight of alkyl-tin stabilizer.

Other feasible embodiments of the treatment can employ adding the calcium into the reactor after anhydrification and then filter the reaction mixture through Celite alone, or with anhydrous Na2SO4, once the carboxylate level has been determined to be optimal. Passing the mixture through a centrifuge prior to filtration is another possible treatment to reduce filtration time.

Various embodiments of the invention have been described; however, it will be evident to those of ordinary skill in the pertinent art that various modifications and changes may be made thereto, and additional embodiments may be implemented, without departing from the broader scope of the exemplary embodiments as set forth in the claims that follow. The specification is accordingly to be regarded in an illustrative rather than a restrictive sense.

What is claimed is:

1. A method comprising reacting an alkyl-tin stabilizer composition having a first level of carboxylate content with a calcium compound, filtering treated stabilizer composition and collecting filtered stabilizer composition with a second level of carboxylate content that is lower than the first level of carboxylate content.

2. The method of claim 1, further comprising adding the filtered stabilizer composition to a polyvinyl chloride composition.

3. The method of claim 1, wherein the alkyl-tin stabilizer composition includes an alkyl-tin thioglycolate stabilizer and there is less alkyl-tin salt of thioglycolic acid present in the second level of carboxylate content than in the first level of carboxylate content.

4. The method of claim 1, wherein the alkyl-tin stabilizer composition includes an alkyl-tin thioglycolate stabilizer selected from the group consisting of butyl-tin thioglycolate stabilizer, methyl-tin thioglycolate stabilizer and octyl-tin thioglycolate stabilizer.

5. The method of claim 1, wherein the calcium compound includes at least one of calcium oxide and calcium hydroxide.

6. The method of claim 1, wherein the filtered stabilizer composition has less coloring than the alkyl-tin stabilizer composition prior to reacting with the calcium compound.

7. The method of claim 1, wherein the filtered stabilizer composition is less cloudy than the alkyl-tin stabilizer composition prior to reacting with the calcium compound.

8. The method of claim 1, further comprising providing at least one of calcium oxide and calcium hydroxide in an amount of 0.25% to 5.0% by weight of the alkyl-tin stabilizer composition for said reacting with the alkyl-tin stabilizer composition.

9. The method of claim 1, wherein said reacting and filtering are carried out with a filter media including at least one of calcium oxide and calcium hydroxide.

10. The method of any of claim 1, wherein said reacting is carried out by adding at least one of calcium oxide and calcium hydroxide to the alkyl-tin stabilizer solution prior to said filtering.

11. The method of any of claim 1, further comprising providing a combination of calcium oxide and calcium hydroxide in a by weight ratio of from 1:1 to 1:5 for said reacting with the alkyl-tin stabilizer composition.

12. The method of claim 1, wherein said reacting is conducted at from approximately 50° C. to approximately 60° C.

13. The method of claim 9, wherein said filter media includes a 5:1:2 by weight ratio of calcium oxide: calcium hydroxide: anhydrous Na2SO4.

14. The method of claim 9, wherein said filter media includes a 1.5:1.5:3:3 by weight ratio of CaO:Ca(OH)2: Na2So4: Celite.

15. The method of claim 2, wherein the alkyl-tin stabilizer composition includes an alkyl-tin thioglycolate stabilizer selected from the group consisting of butyl-tin thioglycolate stabilizer, methyl-tin thioglycolate stabilizer and octyl-tin thioglycolate stabilizer.

16. The method of claim 15, wherein the calcium compound includes at least one of calcium oxide and calcium hydroxide.

17. The method of claim 16, further comprising providing at least one of calcium oxide and calcium hydroxide in an amount of 0.25% to 5.0% by weight of the alkyl-tin stabilizer composition for said reacting with the alkyl-tin stabilizer composition.

18. The method of claim 17, wherein said reacting and filtering are carried out with a filter media including at least one of calcium oxide and calcium hydroxide.

19. The method of claim 18, wherein said filter media includes a 5:1:2 by weight ratio of calcium oxide: calcium hydroxide: anhydrous Na2SO4.

20. The method of claim 16, further comprising providing a combination of calcium oxide and calcium hydroxide in a by weight ratio of from 1:1 to 1:5 for said reacting with the alkyl-tin stabilizer composition.

* * * * *